United States Patent [19]

Cheetham

[11] 4,294,351

[45] * Oct. 13, 1981

[54] CONTAINERS

[76] Inventor: Jeffery J. Cheetham, 5 Brunsdon St., Bayswater, Victoria, Australia, 3153

[*] Notice: The portion of the term of this patent subsequent to Sep. 11, 1996, has been disclaimed.

[21] Appl. No.: 58,260

[22] Filed: Jul. 17, 1979

Related U.S. Application Data

[63] Continuation of Ser. No. 774,950, Mar. 7, 1977, Pat. No. 4,167,228.

[30] Foreign Application Priority Data

May 5, 1976 [AU] Australia .............................. PC5817
Oct. 18, 1976 [AU] Australia .............................. PC7760

[51] Int. Cl.³ ............................................. B65D 25/08
[52] U.S. Cl. ................................................... 206/222
[58] Field of Search ................... 128/218 M; 206/219, 206/222; 215/6, 307, 309, DIG. 8; 222/80, 83, 386; 259/DIG. 20

[56] References Cited

U.S. PATENT DOCUMENTS

| | | | |
|---|---|---|---|
| 3,156,369 | 11/1964 | Bowes et al. | 215/250 X |
| 3,220,588 | 11/1965 | Lipari | 206/222 |
| 3,344,914 | 10/1967 | Bloom et al. | 206/222 |
| 3,603,469 | 9/1971 | Magni | 206/222 |
| 3,785,481 | 1/1974 | Allet-Coche | 206/219 |
| 3,809,225 | 5/1974 | Allet-Coche | 206/220 |
| 3,968,872 | 7/1976 | Carazza | 215/309 |
| 4,167,228 | 9/1979 | Cheetham | 128/218 M |
| 4,195,731 | 4/1980 | Carazza | 206/222 |

Primary Examiner—Stephen P. Garbe
Attorney, Agent, or Firm—William R. Hinds

[57] ABSTRACT

The present invention provides a multi-compartment container designed for storage and transportation in separated condition of the components of a composition, particularly where the components are interactive, and for admixture of the components when required for use. The container comprises a chamber separated into first and second compartments by a partition, wherein the first compartment is arranged to receive a first component of a composition and the second compartment is arranged to receive a second component of the composition, the partition is mounted on the interior of the container and the first compartment is provided with a plunger which is sealingly slidable within the first chamber, is initially mounted in an extended condition so that the innermost end of the plunger defines a wall of the first compartment opposite to the partition and is arranged to be depressed and to separate a portion of the margin of the partition from the interior of the chamber.

7 Claims, 3 Drawing Figures

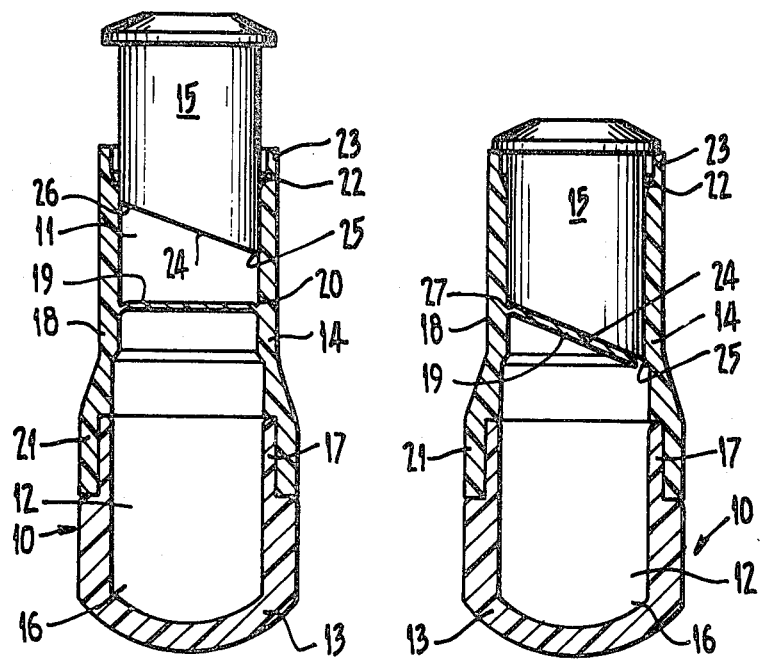
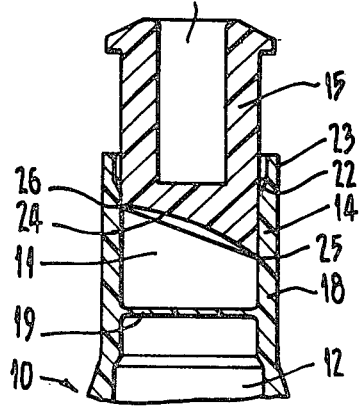

CONTAINERS

This is a continuation of application Ser. No. 774,950 filed Mar. 7, 1977, now U.S. Pat. No. 4,167,228.

The present invention relates to multi-compartment containers.

In U.S. Pat. No. 3,809,225 there is described a container comprising two chambers separated by a partition. A first of the chambers is arranged to receive a first, liquid component of a composition and a second of the chambers is arranged to receive a second component of the composition for admixture with the liquid. The partition is removably located at the junction of the two chambers and is in frictional engagement with the interior of the container. A plunger is initially mounted in extended condition in an end of the first chamber.

The container of U.S. Pat. No. 3,809,225 is designed for storage and transportation of the first and second components of the composition in separated condition in their respective chambers. When it is desired to admix the first and second components, the plunger is depressed with the second chamber lowermost whereby the partition is dislodged and falls into the second chamber together with the first liquid component. The container is then vibrated to cause admixture of the components to form the composition.

The container of U.S. Pat. No. 3,809,225 is stated to be particularly useful for storage, transportation and admixture of dental amalgams wherein the first liquid component is mercury and the second component is a metallic powder. Further, it is stated that for sufficient admixture of the components it is essential that a pestle be present and that the dislodged partition fulfills this function. Still further, the partition is said to be dislodged by a combination of physical contact with the plunger and hydrostatic pressure.

In U.S. Pat. No. 3,731,853 there is described a multi-chamber receptacle for storing and mixing the ingredients of products such as dental preparations, including a chamber in a casing for storing liquid or pasty material and a piston for closing the chamber during initial storage and for then expelling the material from the chamber into a main chamber in a container where the liquid or pasty material will be mixed with a pulverulent ingredient. The casing has a frangible bottom portion or the like adapted to be ruptured for transfer of the liquid or pasty material to the main chamber.

In U.S. Pat. No. 3,739,847 there is described a storing and mixing receptacle including a container forming a first chamber at its lower end for initially storing a first ingredient, a first piston for separating the first chamber from a second chamber, a second piston movable in the second chamber and adapted to transfer a second ingredient from the latter chamber to the first chamber where the ingredients will be mixed. After removal of a closure means from the lower end of the container, the first piston will be actuated to expel the mixture from the receptacle in the form of a ready product such as a dental preparation ready for use.

The receptacles disclosed in U.S. Pat. No. 3,731,853 and U.S. Pat. No. 3,739,847 have fixed partitions which are arranged to be ruptured by exertion of hydraulic pressure by the piston or pistons through the ingredient contained in the respective chamber.

The present invention provides an improved container for transport and storage of components of compositions in separated condition and for use in admixture of the components to form the composition. The container of the present invention has the advantages that it does not rely on a pestle for sufficient admixture of the components and does not rely on hydraulic pressure to bring the components into contact with one another.

According to one aspect of the present invention there is provided a container comprising a chamber separated into first and second compartments by a partition, wherein the first compartment is arranged to receive a first component of a composition and the second compartment is arranged to receive a second component of the composition, the partition is mounted on the interior of the container and the first compartment is provided with means for separating a portion of the margin of the partition from the interior of the container.

In the container of the present invention a portion of the margin of the partition is, in use, separated from the interior of the container to allow the first component to contact the second component. The components are then caused to admix in known manner to form the composition which is then retrieved from the container for use. It is to be noted that only a portion of the margin of the partition is separated from the interior of the container. Thus, the partition is still attached to the interior of the container by the remaining unseparated portion of its margin. Therefore, the partition is not used as a pestle as in the container of U.S. Pat. No. 3,809,225. This is an important and advantageous feature of the present invention as it has been found that the use of a pestle during admixture is not essential for achieving satisfactory results. Further, the presence of a pestle is disadvantageous. For example, it has been found that the pestle tends to become embedded in the composition and has to be manually separated therefrom which is a time consuming and wasteful exercise. This problem arises with all types of composition but is particularly prevalent when admixing components which are of a similar density to the pestle which is typically formed of a plastics material. For example, when admixing dental cements formed from a first liquid component e.g. phosphoric acid, and a second component e.g. zinc oxide powder, it has been found that the cement becomes deposited around the pestle and has to be separated therefrom for use.

The container of the present invention can be used for storage, transportation and admixture of the components of any form of composition but preferably at least one of the components is a liquid. Further, it is particularly useful for use with components which upon admixture interact with one another in some way which is either irreversible or extremely difficult to reverse to form a composition which requires to be used soon after its formation. Examples of such compositions are the aforementioned dental cements and amalgams.

The container of the present invention is particularly useful for storage, transportation and admixture of dental compositions such as dental cements and amalgams. Dental cements typically comprise a liquid component e.g. phosphoric acid, and a solid component e.g. zinc oxide powder while dental amalgams typically comprise a liquid mercury component and a solid component such as a metallic powder.

Preferably, the separating means is in the form of a plunger which is sealingly slidable within the first chamber. Initially the plunger is mounted within the first chamber in an extended condition so that the innermost end of the plunger defines a wall of the first compartment opposite to the partition which defines another wall of the first compartment.

In a preferred embodiment of the present invention the innermost end of the plunger is inclined to the partition such that, upon the plunger being depressed, the leading edge of the plunger contacts the partition adjacent its margin and then separates a portion of the partition from the interior of the container. Most preferably, the innermost end of the plunger has an inclined surface such that continued depression of the plunger causes the partition to be hinged towards the second compartment.

The partition is attached to the interior of the container and may be integrally formed therewith. The partition is weakened at least at the portion thereof to be separated from the interior of the container, or it may be of substantially uniform thickness.

According to a preferred aspect of the present invention there is provided a container comprising means defining a chamber separated into first and second compartments, the first compartment being arranged to contain a first component of a composition and the second compartment being arranged to contain a second component of the composition, wherein the means defining the chamber comprises a wall means having a closed end and an open end, a partition integrally formed with the wall means and a plunger having an inner surface, slidingly and sealingly located in the open end of the wall means with the inner surface spaced from the partition, the first compartment being defined by part of the wall means, the partition and the inner surface of the plunger and the second compartment being defined by the closed end of the wall means and the partition, and the inner surface of the plunger being inclined at an acute angle to the partition and having a leading edge and a trailing edge, whereby upon the plunger being depressed the leading edge of the inner surface first separates a corresponding portion of the margin of the partition from the wall means and then the partition is hinged towards the second compartment by progressive contact with the inner surface and corresponding progressive separation of the margin of the partition from the wall means, the stroke of the plunger being limited by contact of the trailing edge of the inner surface with a corresponding unseparated portion of the margin of the partition.

In this preferred embodiment of the invention a portion of the margin of the partition corresponding with the trailing edge of the inner surface remains attached to the wall means. Thus, the partition is still attached to the wall means during the mixing operation. Further, the partition does not become trapped between the wall means and the side of the plunger. Rather, contact of the trailing edge with the partition limits the stroke of the plunger.

The present invention also provides the containers containing a first component of the composition in the first-compartment and a second component of the composition in the second-compartment.

The present invention will now be described, by way of illustration with reference to the accompanying drawings, in which:

FIG. 1 is a schematic sectional view of a container in accordance with the present invention;

FIG. 2 is a schematic sectional view of the container of FIG. 1 in operated condition; and FIG. 3 is a schematic sectional view of another embodiment of a container in accordance with the present invention.

In FIGS. 1 and 2, there is shown a container 10 comprising means defining a first compartment 11 and a second compartment 12. The container is formed from three components which are a bowl member 13, a substantially cylindrical member 14 and a plunger member 15.

The bowl member 13 comprises wall means defining a receptacle 16 which is substantially circular in cross section, and a circular upstanding flange member 17.

The substantially cylindrical member 14 comprises circular wall means 18 having integrally formed therewith a circular partition member 19 provided with a peripheral groove 20. At its lowermost end as seen in the drawings the wall means 18 is provided with a circular flange 21 of larger diameter than the wall means 18. At the uppermost end the wall means 18 is provided with a shoulder 22 and a relatively thin wall portion 23.

The plunger member 15 is slidingly mounted in the cylindrical member 14 and is provided with sealing means (not shown) so as to provide sealing engagement with the wall means 18. Further, the plunger member is provided with an inner inclined surface 24 having a leading edge 25 and a trailing edge 26.

Typically the components of the container are formed from a plastics material. Further, the components of the container are conveniently formed by extrusion and moulding of plastics material in known manner.

In use, the container is initially used to store and transport the components of a composition in separated form, the composition being formed from a first, preferably liquid component and a second component which may be for example a liquid or a powder.

By way of example, on assembly the second component is placed in the receptacle 16 of the bowl member 13. The cylindrical member 14 is then mounted on and engaged with the bowl member 13 by engagement between the upstanding flange 17 of the bowl member 13 and the circular flange 21 of the cylindrical member 14. Next, the first component of the composition is placed in the cylindrical member 14 and finally the plunger member 15 is slidingly and sealingly mounted in the cylindrical member 14 by the relatively thin wall portion 23, in an extended condition as shown in FIG. 1.

In the assembled condition, the first compartment 11 is defined by a portion of the cylindrical wall 18, the partition 19 and the plunger member 15 and contains the first component. The second compartment 12, which is larger than the first compartment 11, is defined by the bowl member 13, the partition 19 and the remaining portion of the cylindrical wall 18, and contains the second component when it is desired to admix the first and second components, the plunger member 15 is depressed, for example, manually.

This action causes the leading edge 25 of the inclined surface 24 to contact the groove 20 in the partition 19. The partition 19 is thereupon ruptured by the leading edge 25 and a portion of the periphery of the partition 19 becomes separated from the interior of the cylindrical member 14. Upon continued depression of the plunger member 15 progressively greater amounts of the periphery of the partition 15 are separated and the partition 15 is hinged towards the second compartment 12 by contact with the inclined surface 24. Depression of the plunger member 15 is normally continued until the trailing edge 26 of the inclined surface contacts a residual portion 27 of the periphery of the partition 19 which is still attached to the interior of the cylindrical member 14 (as shown in FIG. 2). The rupture and hinged movement of the partition 19 allows the component in the first compartment 11 to fall onto and contact the component in the second compartment 12, when the container is actuated in the upright position shown in the drawings. However, the container need not be actuated in the upright position because, even if the container were actuated in an inverted position the component in the first compartment would be pushed into the second compartment by the inner surface as the plunger is depressed.

If the first component is a liquid the volume of liquid in the first compartment is not normally so great as to prevent contact of the leading edge 25 with the partition 19 upon depression of the plunger 15.

When the components have been contacted the container is placed in a vibrating machine of known type where it is vibrated for a period of time sufficient for admixture to take place. Finally, the bowl member 13 is detached from the cylindrical member 14 and the composition removed therefrom for use.

In FIG. 3 there is shown another embodiment of the present invention which is similar to that shown in FIG. 1. In FIGS. 1 and 3 like reference numerals are used to denote like parts.

In the embodiment shown in FIG. 3, the circular partition member is of uniform thickness. Also, the plunger member 15 has an axial locating hole 15a formed therein at its outer end to assist in assembly of the container 10. Further, the inner surface 24 is concave. For reasons which will be explained hereinafter, this provides enhanced sharpness at the leading edge 25.

The container of this embodiment operates in essentially the same way as the container of FIG. 1 except that there is no peripheral groove adjacent the margin thereof. Thus, the leading edge 25 has to penetrate the full thickness of the partition 19. The provision of a concavity in the inner face 24 enhances the sharpness of the leading edge 25 and thereby facilitates the rupture of the partition 19.

The container of the present invention is particularly useful where it is required to prepare a composition which must be used within a short time of its preparation before the mixed substances have time to interact and make the composition unusable. Further, the container enables the interactive substances to be stored and transported in separated but adjacent condition ready for immediate admixture when required.

The container has been found particularly useful for use with dental cements comprising a liquid component such as phosphoric acid and a powder component such as zinc oxide, and dental amalgams comprising a liquid mercury component and a metallic powder component.

It has been found that the container of the present invention enables the components to be completely admixed since there is no entrapment of liquid or other components in the first compartment. This is avoided by the hinging movement of the partition 19 upon contact with the plunger 15. Also, the partition whilst allowing contact of the component with each other does not become detached from the wall of the container and therefore does not interfere with the mixing process. Further, there is little or no possibility of premature admixture of the components.

The lack of reliance or hydraulic pressure to rupture the partition 19 reduces the possibility of mercury or other liquid being forced past the plunger 15.

The mixed components are easily removed upon separation of the bowl member 13 and cylindrical member 14. Further, the construction of the container 10 lends itself readily to automatic assembly operations.

An important advantage is that the plunger 15 can be actuated by thumb pressure alone and does not require the use of an actuating press.

The present invention will now be described further by the following examples, but it is to be understood that any dimensions and other data contained therein are illustrative only and should not be taken as limiting the scope of the present invention.

EXAMPLE 1

A container 10 in accordance with FIG. 1 of the accompanying drawings was produced. In the container of the example the partition 19 was 0.035 inch thick while groove 20 at its thinnest point was 0.005 inch thick. The first compartment 11 had an internal diameter of 0.3 inch, while the second compartment 12 had an internal diameter of 0.37 inch. The surface 24 was inclined at an angle of 30 degrees to the partition 19.

It has been found that the container of this example gives excellent results when used as described hereinabove for admixture of dental cements and amalgams. Upon application of thumb pressure to the plunger 15 a portion of the partition 19 is separated at the groove 20 from the interior of the container 10 by the leading edge 25. This allows the first component in the first compartment 11 which is typically liquid mercury in the case of a dental cement to fall onto the second component which is typically a metallic powder in the second compartment 12. The plunger 15 is usually depressed until the trailing edge 26 contacts the partition 19 and the partition 19 is hinged toward the second compartment 12 by the inclined surface 24.

Next the capsule is mounted on a vibratory machine in known manner. A typical vibratory machine is marketed under the trade name "Silamat". It has been found that the required mixing time is of the order of 10 seconds when the vibratory machine is oscillating at about 3500 cycles per minute. A fully satisfactory dental amalgam ready for immediate use is obtained upon removing the capsule from the machine and separating the bowl member 13 and the substantially cylindrical member 14.

Similar results are obtained in the preparation of dental cements using a capsule in accordance with this example.

EXAMPLE 2

A container 10 in accordance with FIG. 3 of the accompanying drawings was produced. In the container of the example the partition 19 was 0.013 inch thick. The first compartment 11 had an internal diameter of 0.315 inch, while the second compartment 12 had an internal diameter of 0.37 inch. The surface 24 was plane and inclined at an angle of about 20 degrees to the partition 19.

When the container of this Example is used to produce dental amalgams and cements in the way described in Example 1 fully satisfactory mixed products are obtained.

Modifications and variations such as would be apparent to a skilled addressee are deemed within the scope of the present invention. For example, the first chamber could have a non-circular cross-section such as a square or hexagon cross-section. Also, the plunger 15 can be made sealingly slidable within the cylindrical member 14 by making it a tight fit therein thus avoiding the need for a specifically constructed sealing means.

I claim:

1. A container comprising means defining a chamber separated into first and second compartments, the first compartment being arranged to contain a first component of a composition and the second compartment being arranged to contain a second component of the composition, said means defining the chamber comprising a wall means having a closed end and an open end, a partition extending across the wall means, and a plunger slidingly and sealingly located in the open end of the wall means, said plunger having an inner end surface spaced from the partition, the inner surface of the plunger being inclined at an acute angle to the partition and having a leading edge and a trailing edge movable along said wall means during a depression stroke of the plunger, at least the major portion of the interior surface of said wall means over which the leading and trailing edges of said inner surface of said plunger move during its depression stroke defining a chamber portion of substantially uniform lateral dimensions on both sides of said partition, said first compartment being defined by part of the wall means, said partition and the inner surface of said plunger, and the second compartment being defined by the closed end of the wall means and the partition, whereby upon the plunger being depressed the leading edge of the inner surface first separates a corresponding portion of the margin of the partition from the wall means, and then the partition is hinged toward the second compartment by progressive contact with the inner surface and corresponding progressive separation of the margin of the partition from the wall means, the stroke of the plunger being limited so as to leave an unseparated portion of the margin of the partition.

2. A container as claimed in claim 1 wherein said edges sealingly engage said wall means over substantially the full depression stroke.

3. A container as claimed in claim 1 wherein at least the trailing edge of said plunger sealingly engages said wall means over substantially the full depression stroke.

4. A container as claimed in claim 1 wherein at least said leading edge sealingly engages said wall means over substantially the full depression stroke.

5. A container as claimed in claim 1 wherein said partition is integrally formed with said wall means.

6. A container comprising means defining a chamber separated into first and second compartments, the first compartment being arranged to contain a first component of a composition, and the second compartment being arranged to contain a second component of the composition, wherein the means defining the chamber comprises a wall means having a closed end and an open end, a partition integrally formed with the interior of the wall means, and a plunger having an inner surface slidingly and sealingly located in the open end of the wall means with the inner surface spaced from said partition, the first compartment being defined by part of the wall means, the partition and the inner surface of the plunger, with the inner surface of the plunger lying completely within the wall means in all positions of the plunger so that no part of the first compartment extends beyond the wall means in any direction, the second compartment being defined by the closed end of the wall means and the partition, and the inner surface of the plunger being inclined at an acute angle to the partition and having a leading edge and a trailing edge, whereby upon the plunger being depressed the leading edge of the inner surface first separates a corresponding portion of the margin of the partition from the wall means and then the partition is hinged toward the second compartment by progressive contact with the inner surface and corresponding progressive separation of the margin of the partition from the wall means.

7. A container comprising means defining a chamber separated into first and second compartments, the first compartment being arranged to contain a first component of a composition and the second compartment being arranged to contain a second component of the composition, wherein the means defining the chamber comprises a wall means having a closed end and an open end, a partition extending across the wall means, and a plunger having an inner surface, slidingly and sealingly located in the open end of the wall means with the inner surface spaced from the partition, the first compartment being defined by part of the wall means, the partition, and the inner surface of the plunger, and the second compartment being defined by the closed end of the wall means and the partition, and the inner surface of the plunger being inclined at an acute angle to the partition and having a leading edge and a trailing edge, whereby upon the plunger being depressed the leading edge of the inner surface first separates a corresponding portion of the margin of the partition from the wall means and then the partition is hinged toward the second compartment by progressive contact with the inner surface and corresponding progressive separation of the margin of the partition from the wall means, the stroke of the plunger being limited to contact of the trailing edge of the inner surface with a corresponding unseparated portion of the margin of the partition.

* * * * *